United States Patent [19]

Norval et al.

[11] Patent Number: 5,296,227
[45] Date of Patent: Mar. 22, 1994

[54] ATTRACTANT DECOY FOR CONTROLLING BONT TICKS

[75] Inventors: R. A. I. Norval, Gainesville, Fla.; Daniel E. Sonenshine, Virginia Beach, Va.; Martin I. Meltzer; Michael J. Burridge, both of Gainesville, Fla.

[73] Assignees: Old Dominion University, Norfolk, Va.; The University of Florida, Gainesville, Fla.

[21] Appl. No.: 809,939

[22] Filed: Dec. 13, 1991

[51] Int. Cl.⁵ ............... A01N 25/08; A01N 57/00; A01N 53/00
[52] U.S. Cl. .................. 424/411; 424/78.31; 424/485; 424/405; 424/84; 514/75; 514/65
[58] Field of Search ............ 424/403, 405, 410, 411, 424/84

[56] References Cited

U.S. PATENT DOCUMENTS

| | | | |
|---|---|---|---|
| 4,666,767 | 5/1987 | Von Kohovn et al. | 428/304.4 |
| 4,879,117 | 11/1989 | Rombi | 424/411 |
| 4,888,361 | 12/1989 | Sonenshine et al. | 518/700 |
| 5,008,107 | 4/1991 | Warner | 424/84 |

FOREIGN PATENT DOCUMENTS

| | | | |
|---|---|---|---|
| 2111830 | 7/1983 | United Kingdom | 424/411 |
| 2169805 | 7/1986 | United Kingdom | 424/411 |

OTHER PUBLICATIONS

Schoni et al. J. Insect Physiology 30:613–618, 1984.
Sonenshine et al, 1985, Exp. & Appl. Acarology, 1:23–34.
Norval et al, 1989, Science, 243:364–365.
Norval et al, 1991, Exp. & Appl. Acarology, 13:19–26.

*Primary Examiner*—Thurman K. Page
*Assistant Examiner*—Neil Levy
*Attorney, Agent, or Firm*—Whitham & Marhoefer

[57] ABSTRACT

A decoy which includes the attraction, aggregation and attachment components of bont tick pheromones is used to attract hungry male, female, and nymph bont ticks to a location where an acaricide can kill the ticks. The decoy can be disk shaped and can be attachable to the hair or fur of an animal. The decoy may also be in the form of a tail band decoy where the decoy is used to dispense the pheromones and acaricide on those portions of the host animal's body not normally protected by grooming mechanisms.

8 Claims, 7 Drawing Sheets

| Rabbit | Ticks | Percent Dead on Each Ear | | | | | |
|---|---|---|---|---|---|---|---|
| | | 24 Hours | | 72 Hours | | 120 Hours | |
| | | Right | Left | Right | Left | Right | Left |
| No. 1 w/Decoy | Attached | 8 | 6 | 56 | 34 | 58 | 50 |
| | Free | 6 | 6 | 28 | 36 | 42 | 44 |
| | Total | 14 | 12 | 84 | 70 | 100 | 94 |
| No. 2 w/Decoy | Attached | 6 | 6 | 22 | 38 | 48 | 54 |
| | Free | 2 | 6 | 60 | 34 | 50 | 44 |
| | Total | 8 | 12 | 82 | 72 | 98 | 98 |
| Mean/ear ± S.D. | | 11.5 ± 2.18 | | 77.0 ± 6.08 | | 98.0 ± 2.45 | |
| No. 3 Control | Attached | 0 | 0 | 0 | 0 | 0 | 0 |
| | Free | 2 | 4 | 2 | 4 | 2 | 4 |
| | Total | 2 | 4 | 2 | 4 | 2 | 4 |
| No. 4 Control | Attached | 0 | 0 | 0 | 0 | 0 | 0 |
| | Free | 0 | 4 | 0 | 4 | 0 | 4 |
| | Total | 0 | 4 | 0 | 4 | 0 | 4 |
| Mean/ear ± S.D. | | 2.5 ± 1.66 | | 2.5 ± 1.66 | | 2.5 ± 1.66 | |

FIG.1

| Percentage Killed Ticks at Intervals of Time After Ticks are Released Onto Rabbit Ears | | | |
|---|---|---|---|
|  | 24 Hours | 72 Hours | 120 Hours |
| Rabbits w/Decoy |  |  |  |
| Ticks Attached | 6.5 ± 0.9 | 37.5 ± 12.2 | 50 |
| Ticks Free | 5.5 ± 0.9 | 39.0 ± 12.2 | 49 ± 2.5 |
| Total Killed | 12.0 ± 1.4 | 77.0 ± 6.1 | 99.0 ± 1.2 |
| Rabbits Without Decoy |  |  |  |
| Ticks Attached | 0 ± 0 | 0 ± 0 | 0 ± 0 |
| Ticks Free | 2.5 ± 2.7 | 2.5 ± 2.7 | 2.5 ± 2.7 |
| Total Killed | 2.5 ± 2.7 | 2.5 ± 2.7 | 2.5 ± 2.7 |

FIG.2

|  | Percentage of Ticks Attached After | | | |
|---|---|---|---|---|
|  | 3 Hours | | 24 Hours | |
| Rabbit | Left Ear | Right Ear | Left Ear | Right Ear |
| No. 1 w/Decoy | 40 | 26 | 58 | 50 |
| No. 2 w/Decoy | 40 | 26 | 48 | 56 |
| Mean ± S.D. | 33.0 ± 7.0 | | 53 ± 4.1 | |
| No. 3 Control | 0 | 0 | 12 | 4 |
| No. 4 Control | 0 | 0 | 0 | 8 |
| Mean ± S.D. | 0.0 ± 0.0 | | 6 ± 4.5 | |

FIG.3

|  |  | Number of Ticks Attracted | | | Percent Mortality of Exposed Ticks Hours After Contact With Decoy | | |
|---|---|---|---|---|---|---|---|
| Replicate | Device | Males | Females | Total | 24 | 48 | 72 |
| 1 | Pheromone+ Acaricide | 14 | 9 | 23 | 0.0 | 26.0 | 100 |
|  | Pheromone Only | 4 | 12 | 16 | 0.0 | 0.0 | 0.0 |
|  | Control | 0 | 0 | 0 | 0.0 | 0.0 | 0.0 |
| 2 | Pheromone+ Acaricide | 11 | 6 | 17 | 0.0 | 17.6 | 100 |
|  | Pheromone Only | 4 | 8 | 12 | 0.0 | 0.0 | 0.0 |
|  | Control | 0 | 0 | 0 | 0.0 | 0.0 | 0.0 |
| 3 | Pheromone+ Acaricide | 2 | 6 | 8 | 0.0 | 37.5 | 100 |
|  | Pheromone Only | 5 | 11 | 16 | 0.0 | 0.0 | 0.0 |
|  | Control | 0 | 0 | 0 | 0.0 | 0.0 | 0.0 |

FIG.4

| RANGE | CHEMICAL COMPONENT | Effect on Tick Species | |
|---|---|---|---|
| | | A. hebraeum | A. variegatum |
| | Long-Range Attractants | | |
| Off-host (up to 30 meters) | Benzaldehyde | + | − |
| | 2,6 dichlorophenol | + | + |
| | methyl salicylate | + | + |
| | nonanoic acid | + | + |
| | O-nitrophenol | + | + |
| | | | |
| | Aggregation | | |
| On-host | Phenylacetaldehyde | + | − |
| | 2,6 dichlorophenol | − | + |
| | methyl salicylate | − | + |
| | O-nitrophenol | − | + |
| | | | |
| | Attachment | | |
| On-host | Benzaldehyde | + | + |
| | benzyl alcohol | + | + |
| | 2,6 dichlorophenol | + | + |
| | heptadecane | + | + |
| | methyl salicylate | + | + |
| | O-nitrophenol | + | + |
| | salicylaldehyde | + | + |

FIG.5

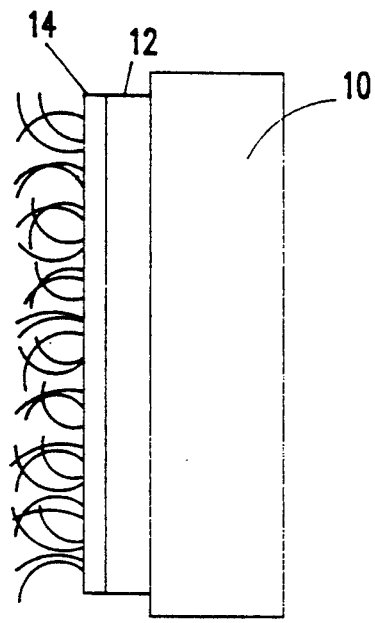
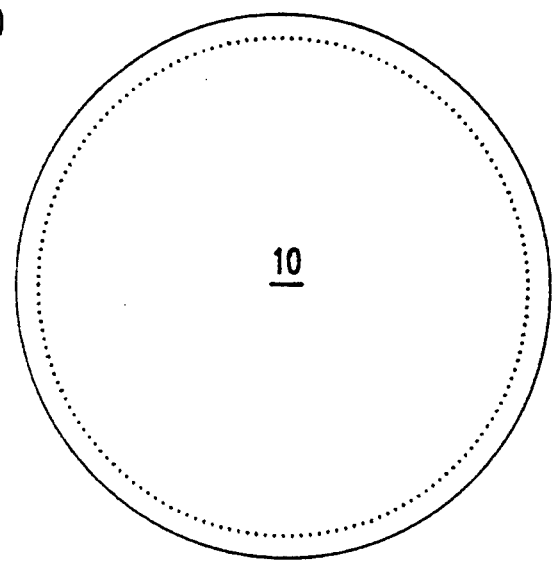
FIG.6  FIG.7
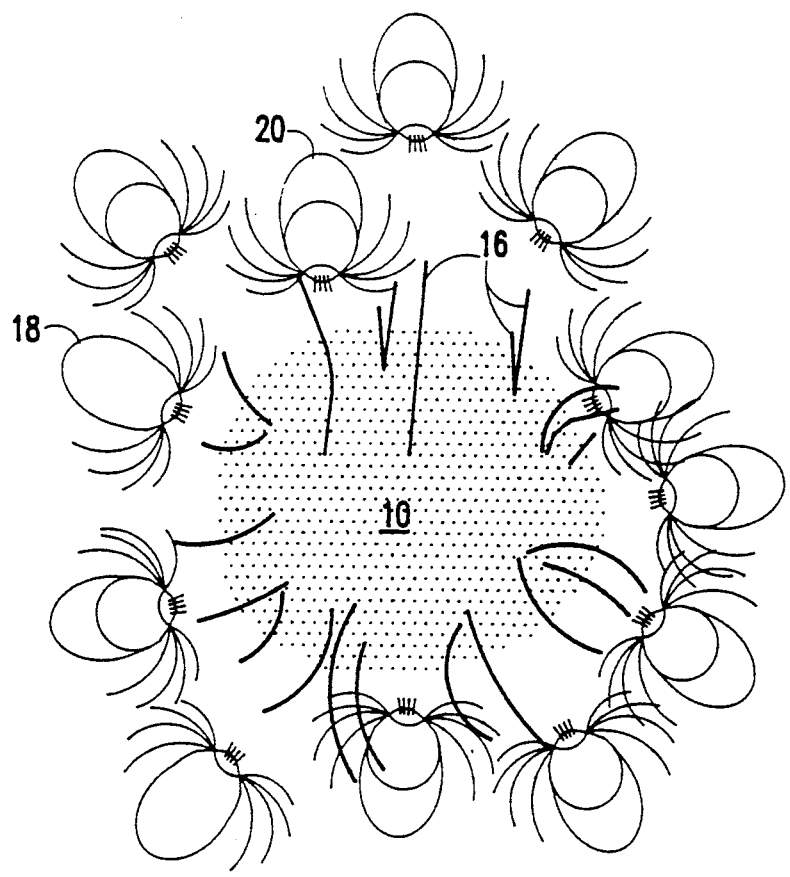
FIG.8

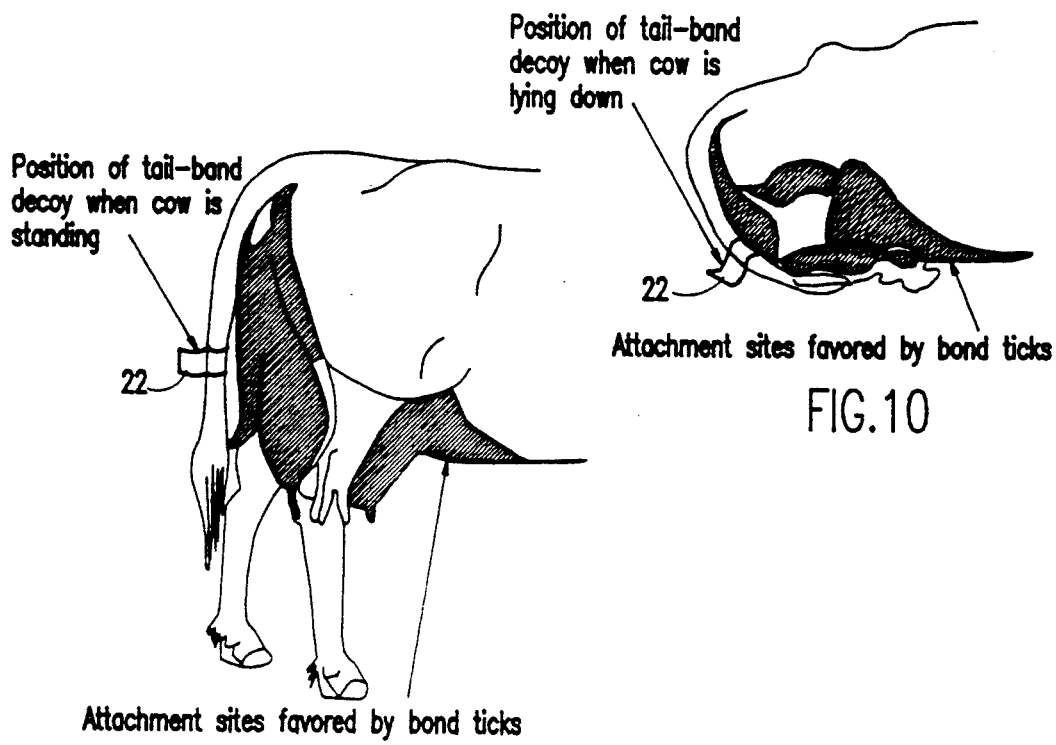
FIG.10
FIG.9
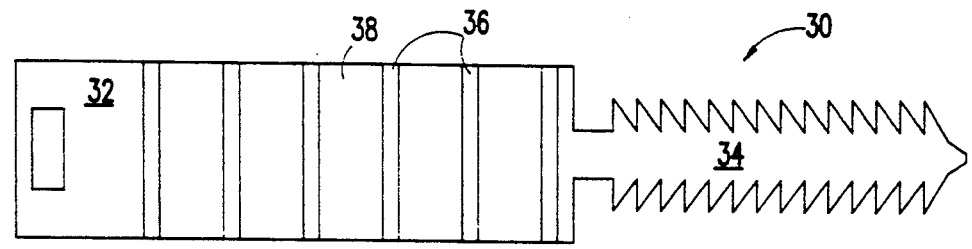
FIG.11
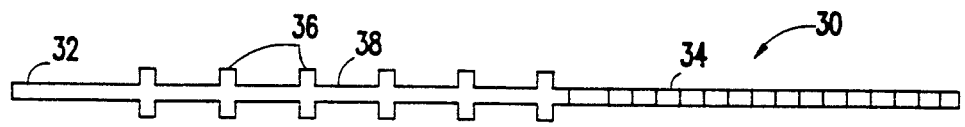
FIG.12
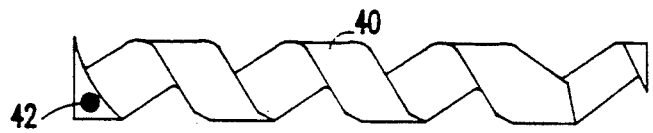
FIG.13

ATTRACTANT DECOY FOR CONTROLLING BONT TICKS

BACKGROUND OF THE INVENTION

1. Field of the Invention

The present invention is generally related to controlling populations of bont ticks.

2. Description of the Prior Art

Protecting livestock from ticks is a major concern of the agriculture industry. Ticks pierce the skin of animals causing infection and are known to spread disease. Bont ticks, a variety of ticks commonly found in Africa and the Caribbean, are known to spread the fatal heartwater disease responsible for the death of many cattle. *Amblyomma variegatum, Amblyomma hebraeum, Amblyomma gemma* and *Amblyomma lepidum* are all members of the bont tick family.

Over the years, many methods have been developed for controlling tick populations. One common practice used in many countries, including developing countries, is to spray the entire animal with a pesticide. Such spraying operations can pose environmental hazards for the surrounding area as well as health hazards for individuals working near the spraying facility. Using decoys in combination with a pesticide is an attractive alternative to spraying the entire animal. Less pesticide is required since the ticks will be attracted by the decoy to the site where the pesticide is located. Many chemical and visual lures have been used in the past with varying degrees of success. For example, U.S. Pat. No. 4,493,161 and U.S. Pat. No. 229,222 show the uses of visual lures shaped like an animal or plant, respectively. Pheromone attractants have also been used in combination with pesticides. For example, U.S. Pat. No. 4,888,361 to Sonenshine et al. discloses a plastic decoy shaped like a female tick which is impregnated with a sex attraction pheromone, mounting pheromone and a pesticide. In Sonenshine et al., the sex attraction pheromone and mounting pheromone were selected to take advantage of feeding and mating characteristics of many ticks wherein a fed male tick will detach from a host in response to an attraction pheromone and attempt to copulate with a female tick in response to a mounting pheromone.

A problem with using decoys is that they must be specific for the pest to be destroyed. If the ticks to be destroyed do not respond to the decoy which is used, the protection scheme will be ineffective. For example, the Sonenshine et al. tick decoy is not likely to be useful in killing bont ticks. Since bont ticks feed in clusters, there is a high probability that a fed male will mate with a female in the cluster rather than leave the cluster and mount a female decoy. Moreover, there are other problems with the Sonenshine et al. device that make it unattractive. First, the Sonenshine et al. decoy only kills male ticks, not female ticks or nymphs. Second, the Sonenshine et al. decoy operates after a male has been fed. Therefore, bont ticks carrying disease will have already infected a host animal before being attracted to a decoy having sex attractant and mounting pheromones.

SUMMARY OF THE INVENTION

It is therefore an object of the invention to provide a decoy specific for bont ticks which can attract hungry male, female, and nymph bont ticks to a location where a pesticide will kill the ticks.

It is another object of the invention to provide a bont tick decoy which may be placed directly on the host or in a remote location.

It is yet another object of the invention to provide a host aided delivery system in the form of a tail band which fits on the tail of a cow.

According to the invention, the pheromones which induce hungry bont ticks to attach and feed on a host have been identified and these pheromones are used to attract ticks to a site where an acaricide (a substance lethal to ticks) will destroy the ticks. The pheromones, as well as an acaricide, are preferably impregnated in a polymer matrix, such as polyvinyl chloride (PVC), to form the decoy. The polymer matrix will slowly release the pheromones and acaricide over time via outgassing, exclusion, or other mechanisms. The pheromones work in combination with $CO_2$ gas to attract all sexes of bont ticks, including males, females, and nymphs, based on a desire to feed. By attaching the decoy to a host animal, or at a location adjacent to host animals, the $CO_2$ gas naturally expelled by the host animal will act in combination with pheromones. If the decoy is to be used at a remote location, a source of $CO_2$, such as dry ice, must be provided. The decoy may be attached to a host animal using adhesives, fasteners or the like. The decoy need not have a specific shape. A particular configuration of the decoy which has been found to be quite beneficial is a tail-band which fits around the tail of the host animal, such as a cow. Natural swishing movements of the tail causes the decoy to contact the udder, groin, and perianal regions which are not ordinarily protected from tick attachment via grooming behavior. As the decoy touches the udder, etc., small amounts of the pheromone and pesticide are transferred to the animal's hide which then attract and kill ticks.

BRIEF DESCRIPTION OF THE DRAWINGS

The foregoing and other objects, aspects and advantages will be better understood from the following detailed description of a preferred embodiment of the invention with reference to the drawings, in which:

FIGS. 1 and 2 are tables showing the ability of decoys with respectively low and high concentrations of attraction-aggregation-attachment pheromone and an acaricide to attract and kill bont ticks;

FIG. 3 is a table showing that high concentrations of the attraction-aggregation-attachment pheromone are effective for attracting bont ticks and that the decoys function similar to pioneer male bont ticks;

FIG. 4 is a table showing the ability of a decoy which includes an attraction-aggregation-attachment pheromone and acaricide to attract and kill unfed ticks from the ground;

FIG. 5 is a table showing the effects of attractant, aggregation, and attachment components of the pheromones on two different species of bont ticks;

FIG. 6 is a side view of a circular decoy showing a host attachment mechanism;

FIG. 7 is a top view of the decoy shown in FIG. 6;

FIG. 8 is a top view of a decoy attached to a host animal with attached and killed male and female ticks;

FIG. 9 is a side view of a cow with a tail band decoy;

FIG. 10 is a side view of the cow of FIG. 9 where the cow is lying down;

FIG. 11 is a top view of one tail band decoy design;

FIG. 12 is a side view of the tail band decoy of FIG. 11; and

FIG. 13 is a side view of a second tail band decoy design.

DETAILED DESCRIPTION OF THE PREFERRED EMBODIMENTS OF THE INVENTION

As explained in Schoni et al., *J. Insect Physiol.*, 30:613-618 (1984), which is hereby incorporated by reference, O-nitrophenol, methyl salicylate, and nonanoic acid are known natural components of the *Amblyomma variegatum* bont tick pheromone. However, heretofore, the exact role of these components with respect to their ability to attract and/or cause aggregation and attachment of bont ticks was unknown. In addition, Schoni et al. did not contemplate using these pheromones in combination with an acaricide as a decoy to attract and kill bont ticks.

In the present invention, numerous components of the *Amblyomma variegatum* and *Amblyomma hebraeum* bont tick pheromones have been identified and characterized according to their mode of operation. An attraction-aggregation-attachment pheromone has been developed, which, when combined with an acaricide, provides an effective means of destroying hungry bont ticks. The attraction-aggregation-attachment pheromone is so named because it includes a long-range "attraction" component and short-range "aggregation" and "attachment" components. The "attraction" component, which is active for up to thirty meters, attracts bont ticks, including males, females and nymphs from a long range to move to a feeding cluster of other feeding bont ticks. The "aggregation" component, which is effective for a short range on-host, causes the ticks to aggregate in a cluster and stop moving. The "attachment" component, which is also effective for a short range on-host, causes the ticks to insert their mouthparts into the skin of the host and start feeding. The aggregation and attachment components also encourage the ticks to remain in the vicinity of the pheromone source, thereby maximizing the time that the ticks are in contact with the acaricide. The attraction-aggregation-attachment pheromone and the acaricide are impregnated in a plastic matrix to form a decoy. Preferably, the decoy releases the components slowly from the matrix, thus providing extended periods of protection to agricultural livestock.

It has been determined that the attraction-aggregation-attachment pheromone is emitted by feeding male bont ticks and attracts all unfed male, female, and nymph bont ticks. Gas chromatography-mass spectroscopy was used to confirm that O-nitrophenol and methyl salicylate are present in the pheromone and to quantify the high levels in both *Amblyomma variegatum* and *Amblyomma hebraeum*. Specifically, *Amblyomma variegatum* has 5941.3 ng/tick of O-nitrophenol and 56.4 ng/tick of methyl salicylate, and *Amblyomma hebraeum* has 287.4 ng/tick O-nitrophenol and 19.6 ng/tick methyl salicylate (Lusby et al., in manuscript). Other volatile compounds which have been identified in bont ticks include benzyl alcohol and benzaldehyde.

The acaricide can be an organophosphorous compound, pyrethroid compound, or other suitable compound which can be slowly released from a plastic matrix material. Particular acaricides which may be used include Propoxur available from Zoecon, Inc. of Texas and Permethrin available from FMC corporation of Illinois. The plastic matrix material may be nylon, polyvinyl chloride (PVC), or other suitable materials which can be impregnated with pheromones and acaricides and which are capable of slowly releasing the pheromones and acaricides over time. The decoys may be fabricated by mixing together in liquid form, the pheromone, the acaricide, and the matrix material compounds necessary to create a solid resin. Each decoy is then produced from the mixture by molding them in the desired shape using a metal or ceramic mold, and heating the mixture in the mold above the fusion temperature.

The amounts of the pheromone, acaracide, and plastic matrix forming materials are chosen such that a sufficient amount of the pheromone which is capable of attracting bont ticks will be released over time to attract hungry bont ticks and a sufficient amount of the acaracide will be released over time to kill the bont ticks once they have attached and begun to feed. As is pointed out in Schoni et al., *J. Insect Physiol.*, 30:613-618 (1984), *Amblyomma variegatum* ticks responded to test samples of a synthetic pheromone delivered in drops of ether onto a plug of cotton wool at 20 ng/day O-nitrophenol, 10 ng/day methyl salicylate, and 80 ng/day nonanoic acid; however, the ticks are non-responsive below these threshold levels. Schoni et al. also pointed out that the *Amblyomma variegatum* ticks respond well to concentrated mixtures of bont tick pheromones, e.g., 2 µg/day O-nitrophenol, 1 µg/day methyl salicylate, and 8 µg/day nonanoic acid.

As an example, 400 suitable decoys within the practice of the invention, each weighing 1 gram, are prepared by mixing 400 grams of PVC powder, 240 ml of dioctyl phthalate (DOP) plasticizer, 12 ml of stabilizer (Mark RFD:organo barium zinc obtained from Argus Division of Witco Corp. of New York), 6 ml of viscosity reducing agent (termed Drapex 6.8, available from Argus), and one percent by weight of each of the final mixture of the following biologically active ingredients: benzyl alcohol, benzaldehyde, heptadecane, 2-methyl propanoic acid, methyl salicylate, nonanoic acid, O-nitrophenol, phenylacetaldehyde and salicylaldehyde. In addition, 2,6-dichlorophenol at 0.2% weight per volume (w/v) of the final mixture is added with the biologically active ingredients. Next, a pesticide such as 10 grams of Propoxur, Permethrin or another synthetic pyrethroid is added. The mixture is stirred until thoroughly mixed, poured into a suitable mold, and then heated in an oven at 140° C. for twenty minutes to cure the plastic matrix material. The mold may be such that a flat disk 7-10 mm in diameter and 5-7 mm thick is formed. Experience with this procedure has shown that approximately 82% of the active ingredients remain the PVC plastic after mixing, heating, polymerizing and cooling.

Tests performed on decoys manufactured according to the above method using molecular sieves and gas chromatographic assays of the molecular sieve extracts showed that the active ingredients and the pesticide emerge from the plastic PVC matrix in sufficient concentrations to effectively attract and kill bont ticks. The active ingredients released by the plastic matrix material were captured by molecular sieve material deposited in a sealed petri dish adjacent to a one gram sample of decoy. The identity of the active ingredients was verified by extracting the molecular sieve material in hexane/diethyl ether (50:50 v/v), and injecting the extract into the gas chromatograph. O-nitrophenol and methyl salicylate were observed and coeluted with authentic standards, confirming their identity. Collections and identification of O-nitrophenol and methyl salicylate were made at weekly intervals. O-nitrophenol and methyl salicylate were found to emerge at an average rate of about 1.4% per day each. Decoys made by the above procedure which were held at 25° C. in a laboratory hood lost O-nitrophenol at a consistent rate over a ten week period. Because the rate of loss of the synthetic pheromone was steady, longer periods of activity should be achieved with decoys having greater amounts of the biologically active compounds. Assuming the empirically measured release rate of 1.4% per day applies to all active ingredients, a one gram decoy will emit 114.8 micrograms of each active ingredient per day (or about 4.8 micrograms per hour). Hence, the amounts of the biologically active compounds that make up the attraction-aggregation-attachment pheromone which are emitted on a daily basis by the decoys formed according to the above method are much greater than the threshold levels identified by Schoni et al., *J. Insect Physiol.*, 30:613-618 (1984).

The activity of the decoys have been examined on animals. Specifically, 250 mg disk shaped decoys fabricated in a manner similar to the above were attached to the ears of rabbits using glue and, following attachment and drying, unfed *Amblyomma hebraeum* ticks (25 males and 25 females) were released onto each ear and confined to the ears using ear bags. A first formulation of the decoys had a low concentration of the attraction-aggregation-attachment pheromone, e.g., 80, 20, and 160 mg of O-nitrophenol, methyl salicylate and nonanoic acid per 100 grams total weight of the decoy. A second formulation of the decoys had a high concentration of the attraction-aggregation-attachment pheromone, e.g., 800, 200, and 1,600 mg of the same materials per 100 grams total weight of the decoy. Each of the first two formulations included 10% by weight of the acaricide Propoxur, which is available from Zoecon, Inc. of Texas. A third formulation included the same constituents as in the second formulation; however, no acaricide was included in the third formulation. FIGS. 1-3 summarize the results with each of the formulations.

FIG. 1 shows the percentage death of tick results at timed intervals after release of the ticks (25 males and 25 females on each ear) for two rabbits having decoys with the low concentration of the attraction-aggregation-attachment pheromone in each ear, and the results for two control rabbits, neither of which has a decoy in either ear. From FIG. 1, it can be seen that with low concentrations of the attraction-aggregation-attachment pheromone, attachment occurred gradually on the ears of the rabbits which had the decoys. Little attachment occurred after twenty four hours and the percentage of dead ticks at twenty four hours was 11.5% for the ticks with the decoys versus only 2.5% on the control rabbits. After the twenty four hour period, the rate of attachment and tick death increased rapidly. Many ticks failed to attach to the rabbits with decoys, but the ticks were killed anyway. This suggests the ticks died before they could complete attachment. Most ticks (77%) died within seventy hours and virtually all were dead after one hundred and twenty hours (98%). The number of ticks which died on the control rabbits was insignificant and did not increase with time.

FIG. 2 is similar to FIG. 1 and shows the percentage of killed ticks at intervals of time after ticks are released onto the rabbit's ears, except the decoys used on the rabbits in FIG. 2 had the high concentration of the attraction-aggregation-attachment pheromone, e.g., 800 mg O-nitrophenol, 200 mg methyl salicylate, and 1600 mg nonanoic acid. The results are similar to that shown in FIG. 1, indicating that there is no effect due to concentration. Specifically, increasing the concentration does not repel the ticks and does not kill the ticks any faster. However, increasing the concentration of the attraction-aggregation-attachment pheromone composition can prolong the time a decoy will be useful.

FIG. 3 shows the percentage attachment results for the ticks at timed intervals after their release on two rabbits having the high concentration formulation without the acaricide and on two control rabbits. FIG. 3 demonstrates the ability of the bont tick decoys to induce attachment by live ticks. Since no acaricide was used, the percentage attachment was not reduced by death of the ticks. Within as little as three hours, an average of 33% of the ticks had attached on the rabbits having the decoys, whereas none had attached to the controls. After twenty four hours, 53% of the ticks had attached on the rabbits having the decoys, versus only 3% on the controls. Hence, the results show that the decoys function in a manner similar to the pioneer male bont ticks which first attach to a host and then emit the attraction-aggregation-attachment pheromone which attracts other hungry males, females and nymphs.

FIG. 4 shows results for the number of ticks attracted to a decoy made in a manner similar to that described above for the high concentration attraction-aggregation-attachment formulation except that the acaricide used was 5% by weight of flumethrin, a synthetic pyrethroid available from Bayer of Germany, and the percent mortality of the ticks which contacted the decoys at timed intervals after contact where the decoys were placed in and around fenced cattle. FIG. 4 shows that no ticks were attracted to control plastic disks, but that a large number of ticks were attracted to decoys which included the attraction-aggregation-attachment pheromone. All ticks which contacted a decoy with the flumethrin acaricide died within seventy two hours after contact.

As is explained in Norval et al., *Exp. Appl. Acarol*, 7:171-180 (1989), which is herein incorporated by reference, bont tick pheromones require $CO_2$ to attract bont ticks. It is envisioned that the decoys according to the present invention will be fabricated such that they are attachable to host animals. Hence, the $CO_2$ naturally expelled by the host animal will be used to activate the attraction-aggregation-attachment pheromone. However, it should be understood that the decoys can be placed at locations not on the host. For example, FIG. 4 shows favorable test results where decoys were placed in and around a fenced yard for cattle. If $CO_2$ emitting animals are not close by, an artificial $CO_2$ source can be used (e.g., dry ice).

FIG. 5 classifies each of the chemical components which may be used in the attraction-aggregation-attachment pheromone of the present invention. The categories in FIG. 5 were empirically determined. Long range attractants include: benzaldehyde, 2,6 dichlorophenol, methyl salicylate, O-nitrophenol and nonanoic acid. These attractant components are effective for up to a 30 meter range. Aggregation components include: phenylacetaldehyde, 2,6 dichlorophenol, methyl salicylate, and O-nitrophenol. Attachment components include: benzyl alcohol, benzaldehyde, 2,6 dichlorophenol, methyl salicylate, salicylaldehyde, heptadecane, and O-nitrophenol. As can be seen from FIG. 5, some of the components of the composition can serve all three functions (e.g., attraction, aggregation, and attachment). Including several different components to form a synthetic attraction-aggregation-attachment pheromone will enhance the effectiveness of a decoy used for killing bont ticks. In particular, FIG. 5 shows that some aggregation pheromone components are effective for one species of bont tick, but not another. For example, phenylacetaldehyde causes aggregation of *A. hebraeum*, but not *A. variegatum*. The same is true for some long-range attractants. By providing more than one long-range attractant or aggregation pheromone component, the decoy produced will be useful for a wider number of bont ticks Other iodinated or chlorinated phenols could be substituted or added to the pheromone within the practice of the invention.

FIGS. 6 and 7 show a circular decoy 10 prepared as described above and includes an attraction-aggregation-attachment pheromone and an acaricide impregnated in a matrix material such as polyvinylchloride. The decoy 10 is approximately 5-8 mm in diameter and weighs between 250 mg to 1 g. An adhesive material 12 is used to secure a Velcro ®-type fastener 14 to the decoy. The fastener 14 should be suitable for attachment to the hair of an animal that needs to be protected from bont tick infestation. For example, FIG. 8 shows the decoy 10 attached to the hair 16 of an animal with a cluster of attracted ticks lying dead there beside. FIG. 8 emphasizes that both male 18 and female 20 bont ticks are attracted by the attraction-aggregation-attachment pheromone in the decoy 10. While FIG. 6 shows a fastener 14 attached to the decoy 10, it should be understood that other means could be used to connect the decoy to an animal. For example, the data presented in FIGS. 1-3 was developed by attaching the decoy 10 to the ears of rabbits using glue. In addition, the decoy 10 could be affixed to the collar of an animal.

As discussed above in conjunction with FIG. 4, a decoy like that shown in FIG. 6 could be placed off-host on the ground near the livestock so that the $CO_2$ from the livestock can still be used to act in combination with the synthetic pheromones in the decoy. A particularly good decoy for this purpose would use candle wax instead of plastic as the slow release matrix material. Wax is advantageous because it is relatively inexpensive and often more readily available in some developing countries than plastics. For each wax based decoy, 30 grams of candle wax is gently heated until molten. The wax is removed in its molten state from the heat source and the biologically active components are added in amounts equal to 1% each by weight to the final mixture. Then the acaricide (e.g., Permethrin or another synthetic pyrethroid) is added to 5% by weight of the final mixture. The mixture is thoroughly stirred and then poured into a container for molding (e.g., a petri dish). Once cooled and hard, the resultant wax disc can be removed from the container and is ready for field use.

FIGS. 9 and 10 show the use of a tail band decoy 22 which includes the attractant-aggregation-attachment pheromone and acaricides of the present invention, as discussed above, to control bont ticks on cattle. It has been found that the natural grooming techniques of cattle tend to remove ticks from most of their bodies (Norval, *Insect Sc. & its Application*, in press (1991)). However, the rear regions of the cow, including the udder, groin, and perianal region, all of which are shaded in grey in FIGS. 9 and 10, tend not to be properly groomed, hence they are a favored attachment site for bont ticks. By attaching a tail band decoy 22 towards the mid-section of the cow's tail, the natural swishing motions of the tail and the method by which a cow normally tucks its tail under its hindquarters while lying down are used for dispensing the pheromone and acaricide on the unprotected regions of the cow's rear end. Bont ticks would then be attracted to these regions and be killed by the acaricide.

FIGS. 11 and 12 show a relatively flat tail band decoy 30 which has a buckle end 32 and a ridged connector end 34. The tail band decoy 30 is wrapped around the cow's tail and the ridged connector end 34 is slipped through the buckle end 32 until the tail is firmly gripped. Upstanding ribs 36 in middle region 38 aid in gripping the tail and are preferably positioned on both sides of the tail band decoy so that it may be wrapped around the tail in either a clockwise or counterclockwise orientation. The spaces between the ribs 36 help assure that blood flow in the tail is not unduly restricted. FIG. 13 shows an alternative tail band decoy 40 that is spiral in shape. The spiral character of the decoy 40 will perform substantially the same gripping function as the ribs 36 in the FIG. 11 tail band decoy 30. Likewise, the spacing between the spirals will assure blood flow is not restricted. An aperture 42 can be provided for connecting a fastener to the decoy 40. It will be apparent to those skilled in the art that there are many alternative designs which could be used for the tail band decoy. In addition, alternative methods of securing the tail band decoy, such as using adhesives or adhesive tape, could be employed.

The tail band decoy concept, where the pheromone and acaricide are dispensed on only the areas which need protection, can be adapted for use on other animals which don't have thickened tail brushes, e.g., goats, sheep, and dogs. For example, the decoys could be placed around the upper part of the hind legs of these animals, whereby the knee joints would prevent the decoys from falling off. Alternatively, the decoys could be placed around the necks of such animals.

Ten tail-band decoys like that shown in FIGS. 11 and 12, each weighing approximately 18 grams, may be fabricated by preparing the matrix material by mixing 200 grams of PVC powder, (Plastisol, available from the B. F. Goodrich Technical Center), 120 ml of plasticizer, (dioctyl phthalate (DOP), available from Aldrich Chemical Company), 6 ml of stabilizer (Mark RFD: organo barium-zinc, available from Argus Division, Witco Corporation) and, 3.0 ml viscosity reducing reagent (Drapex 6.8, available from Argus Division, Witco Corporation). To this, the following biologically active molecules comprising the attraction-aggregation-attachment pheromone are added, each at 1% by weight of the final mixture: benzyl alcohol, benzaldehyde, 2-methylpropanoic acid, methyl salicylate, nonanoic acid, heptadecane, and, O-nitrophenol. In addition, 2,6 -dichlorophenol at 0.2% w/v of the final mixture is added. A pesticide is then added, for example 20 grams of Permethrin or some other synthetic pyrethroid in a similar concentration. The mixture is stirred until thoroughly mixed, poured into a mold, and then heated in an oven at 160° C. for 30 minutes to cure the resin. The choice of resin, the amount of plasticizer, and the fusing temperature may be varied to alter the consistency of the final product. The tail band decoy should be a strong, rubber consistency and capable of resisting tearing, breaking, or cutting by pulling, twisting or biting actions of the host animal.

While the invention has been described in terms of its preferred embodiments where a pheromone composition specific for bont ticks and an acaricide are impregnated in a decoy and where the decoy is connectable to a host animal, those skilled in the art will recognize the invention can be practiced with considerable modification within the spirit and scope of the appended claims.

Having thus described our invention, what we claim as new and desire to secure by Letters Patent is as follows:

1. A method for protecting an animal from bont ticks comprising the steps of:
   providing a decoy which includes
   (i) a pheromone composition having 1% by weight each of said decoy of O-nitrophenol and methyl salicylate; 0.2% by weight in volume of said decoy of 2,6-dichlorophenol; and 0.1% by weight of phenylacetaldehyde;
   (ii) an acaricide selected from the group consisting of organophosphorous compounds and pyrethroid compounds; and
   (iii) a matrix material selected from the group consisting of polyvinylchloride, nylons and waxes, said matrix material being impregnated with said pheromone composition, and said acaricide as 5-10% by weight of said decoy, said matrix material capable of releasing quantities of said composition and said acaricide over time which are sufficient to attract and kill said male, female, and nymph bont ticks; and
   securing said decoy to a host animal that exhales $CO_2$ and needs to be protected against bont tick infestation.

2. The method according to claim 1 of securing said decoy as a tail band to said animal's tail.

3. The method of claim 2, securing said decoy as a tail band having a buckled end and a connector end connectable to said buckled end.

4. A decoy for protecting an animal from bont ticks, comprising:
   a pheromone composition having 1% by weight of said decoy of each of O-nitrophenol and methyl salicylate; 0.2% by weight in volume of said decoy of 2,6-dichlorophenol; and 0.1% by weight of said decoy of phenylacetaldehyde;
   an acaricide of 5-10% by weight of said decoy selected from the group consisting of organophosphorous compounds and pyrethroid compounds;
   a polyvinylchloride, nylon or other resin material, said polyvinylchloride, nylon or resin material being impregnated with said pheromone composition and said acaricide; and
   a means for securing said decoy to the tail of an animal which exhales $CO_2$.

5. A decoy for protecting an animal from bont ticks, comprising:
   a pheromone composition having 1% by weight of said decoy of each of O-nitrophenol and methyl salicylate; 0.2% by weight in volume of said decoy of 2,6-dichlorophenol; and 0.1% by weight of said decoy of phenylacetaldehyde;
   an acaricide of 5-10% by weight of said decoy selected from the group consisting of organophosphorous compounds and pyrethroid compounds;
   a wax material, said wax material being impregnated with said pheromone composition and said acaricide; and
   a means for securing said decoy to the tail of an animal which exhales $CO_2$.

6. The bont tick decoy as recited in claim 4 wherein said securing means is an adhesive.

7. The bont tick decoy as recited in claim 4 wherein said securing means is a fastener attachable to hair and fur.

8. A method for protecting an animal from bont ticks comprising the steps of:
   providing a tail band decoy which includes
   (i) a pheromone composition having 1% by weight of said decoy of each of O-nitrophenol and methyl salicylate; 0.2% by weight in volume of said decoy of 2,6-dichlorophenol; and 0.1% by weight of phenylacetaldehyde;
   (ii) an acaricide selected from the group consisting of organophosphorous compounds and pyrethroid compounds; and
   (iii) a matrix material selected from the group consisting of polyvinylchloride, nylons and waxes, said matrix material formed in the shape of a tail band and said matrix material being impregnated with said pheromone composition, and said acaricide as 5-10% by weight of said decoy, said matrix material capable of releasing quantities of said composition and said acaricide over time which are sufficient to attract and kill said male, female, and nymph bont ticks; and
   securing said tail band decoy to the tail of a host animal that exhales $CO_2$ and needs to be protected against bont tick infestation.

* * * * *

UNITED STATES PATENT AND TRADEMARK OFFICE
CERTIFICATE OF CORRECTION

PATENT NO. : 5,296,227
DATED : March 22, 1994
INVENTOR(S) : R.A.I. Norval, Daniel E. Sonenshine, Martin I. Meltzer, Michael J. Burridge, Conrad E. Yunker It is certified that error appears in the above-indentified patent and that said Letters Patent is hereby corrected as shown below:

Title Page: "[75] Inventors: R.A.I. Norval, Gainesville, Fla.; Daniel E. Sonenshine, Virginia Beach, Va.; Martin I. Meltzer; Michael J. Burridge, both of Gainesville, Fla." should read --R.A.I. Norval, Gainesville, Fla.; Daniel E. Sonenshine, Virginia Beach, Va.; Martin I. Meltzer; Michael J. Burridge, both of Gainesville, Fla.; Conrad E. Yunker, Causeway, Zimbabwe.--

Title Page: [22] Filed Dec. 13, 1991 should read --[22] Filed Dec. 18, 1991. (under CFR 1.47)--

Signed and Sealed this

Thirteenth Day of June, 1995

Attest:

BRUCE LEHMAN

*Attesting Officer*  *Commissioner of Patents and Trademarks*